(12) United States Patent
Alam

(10) Patent No.: US 10,925,875 B2
(45) Date of Patent: Feb. 23, 2021

(54) METHODS OF TREATING STEROID RESISTANT DISEASES AND CONDITIONS

(71) Applicant: National Jewish Health, Denver, CO (US)

(72) Inventor: Rafeul Alam, Aurora, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 16/255,494

(22) Filed: Jan. 23, 2019

(65) Prior Publication Data

US 2019/0224203 A1 Jul. 25, 2019

Related U.S. Application Data

(60) Provisional application No. 62/620,582, filed on Jan. 23, 2018.

(51) Int. Cl.
| | | |
|---|---|---|
| *A61P 29/00* | (2006.01) | |
| *A61P 37/08* | (2006.01) | |
| *A61P 11/06* | (2006.01) | |
| *A61K 9/00* | (2006.01) | |
| *A61K 31/519* | (2006.01) | |
| *C12Q 1/6806* | (2018.01) | |
| *C12Q 1/686* | (2018.01) | |
| *C12Q 1/6883* | (2018.01) | |

(52) U.S. Cl.
CPC .......... *A61K 31/519* (2013.01); *A61K 9/0014* (2013.01); *A61K 9/0019* (2013.01); *A61K 9/0053* (2013.01); *A61K 9/0073* (2013.01); *A61P 11/06* (2018.01); *A61P 29/00* (2018.01); *A61P 37/08* (2018.01); *C12Q 1/686* (2013.01); *C12Q 1/6806* (2013.01); *C12Q 1/6883* (2013.01); *C12Q 2600/106* (2013.01); *C12Q 2600/112* (2013.01); *C12Q 2600/118* (2013.01); *C12Q 2600/158* (2013.01)

(58) Field of Classification Search
CPC ............ A61P 29/00; A61P 37/08; A61P 11/06
See application file for complete search history.

(56) References Cited

U.S. PATENT DOCUMENTS

| | | |
|---|---|---|
| 2014/0227372 A1 | 8/2014 | Missiaglia et al. |
| 2015/0377884 A1 | 12/2015 | Leung et al. |
| 2016/0282363 A1 | 9/2016 | Alam |

FOREIGN PATENT DOCUMENTS

WO WO2018/058029 * 3/2018

OTHER PUBLICATIONS

Ren et al. "Small-Molecule Modulators of Methyl-Lysine Binding for the CBX7 Chromodomain," Chemistry & Biology, Feb. 2015, vol. 22, No. 2, pp. 161-168.
International Search Report and Written Opinion for International (PCT) Patent Application No. PCT/US19/14799, dated Apr. 30, 2019 12 pages.
International Preliminary Report on Patentability for International (PCT) Patent Application No. PCT/US2019/014799, dated Aug. 6, 2020 9 pages.

* cited by examiner

*Primary Examiner* — Barbara P Badio
(74) *Attorney, Agent, or Firm* — Sheridan Ross P.C.

(57) ABSTRACT

Disclosed herein are methods treating and identifying a subject having a steroid resistant disease or condition.

2 Claims, 14 Drawing Sheets

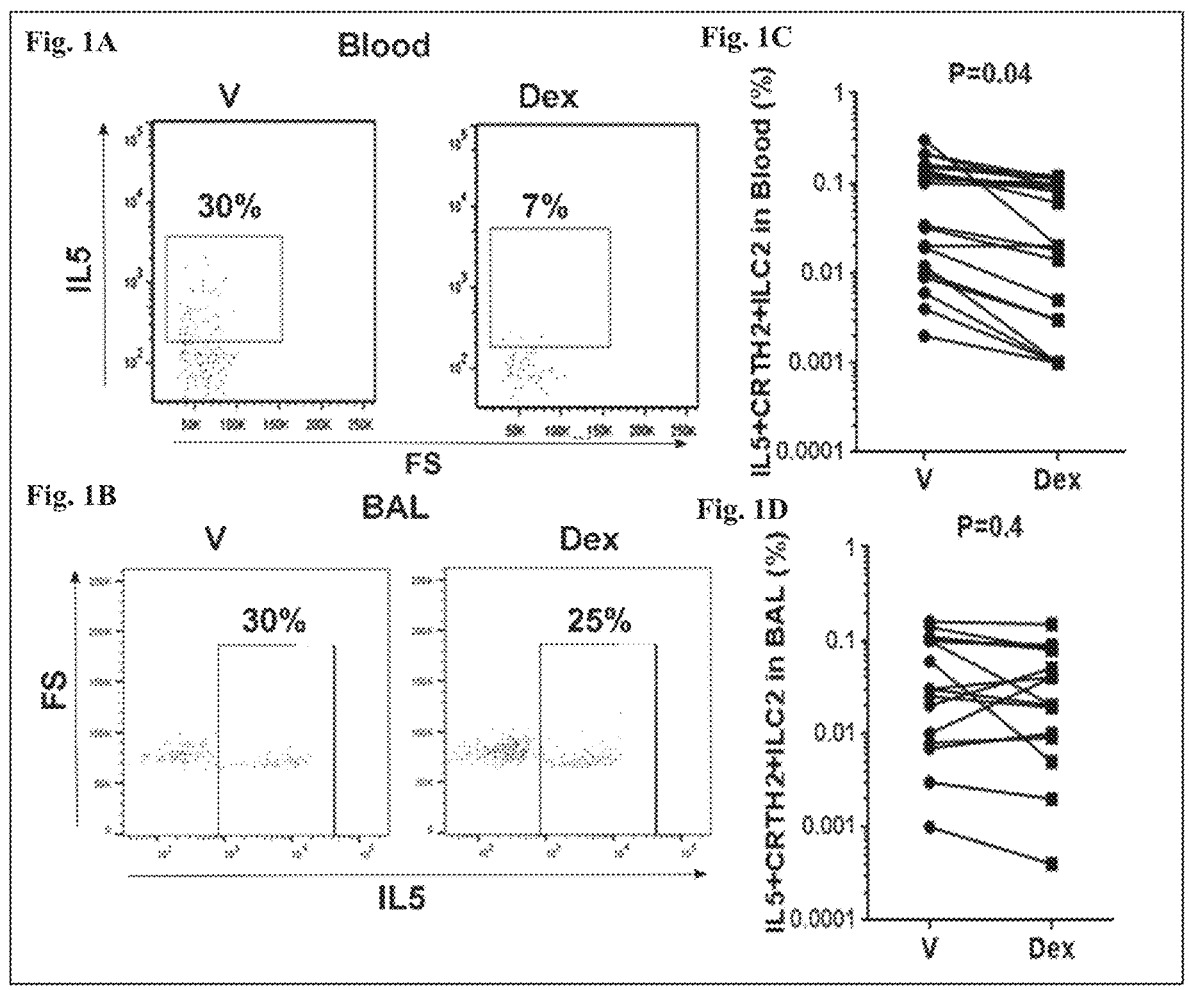

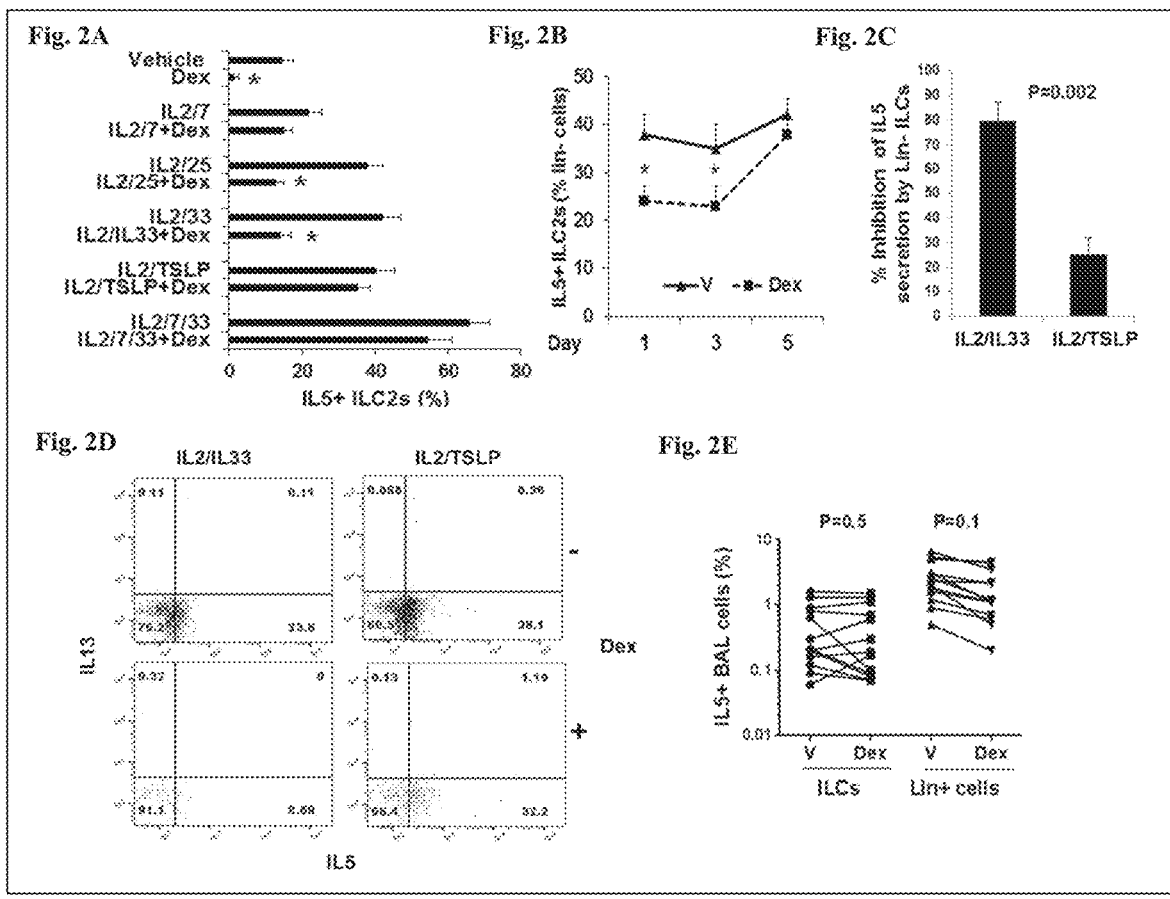

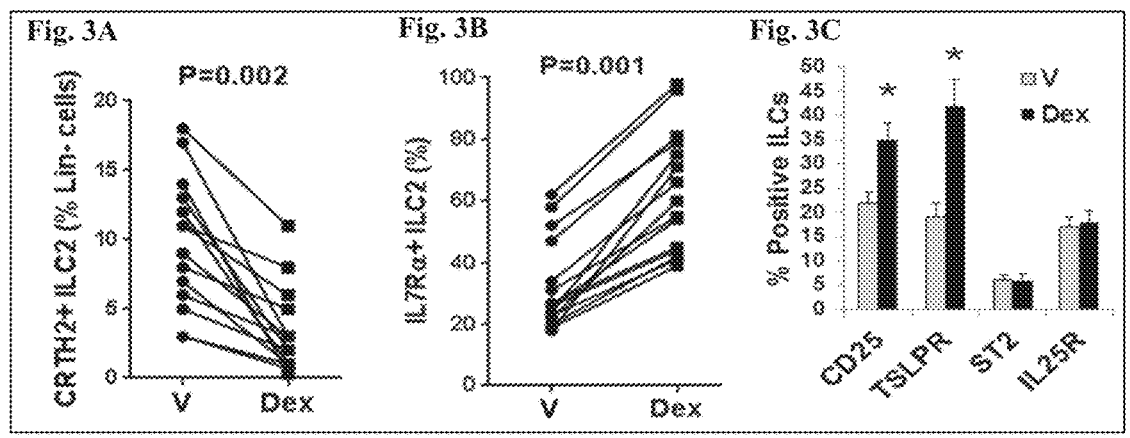
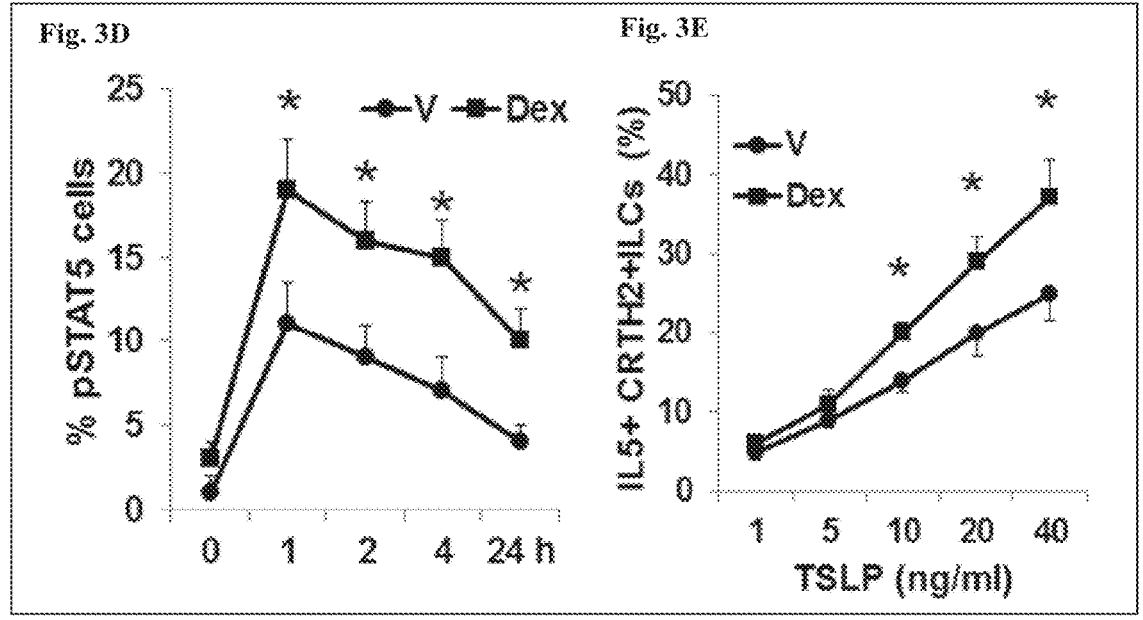

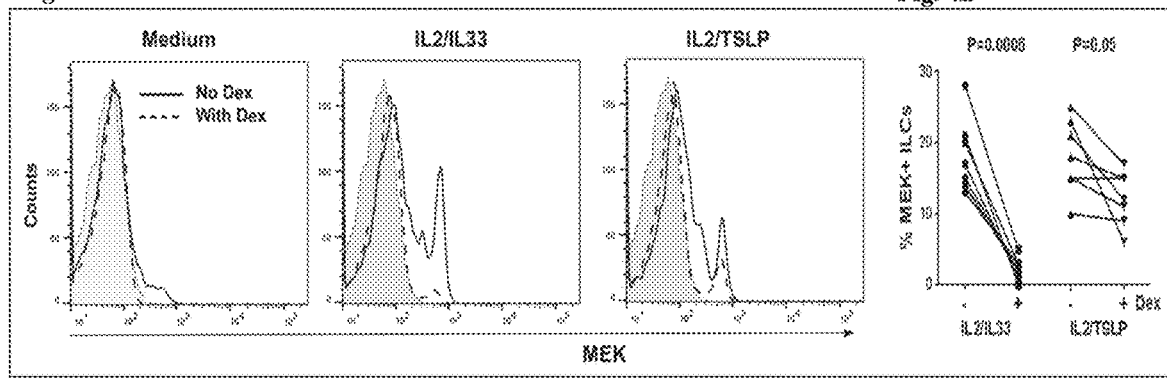
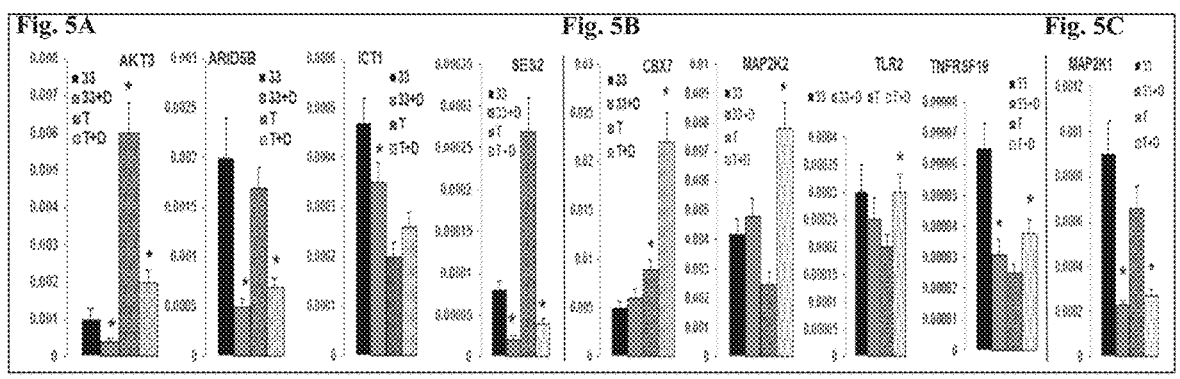

Fig. 12A  IN challenge Alt+DMSO/Alt+MS37452
Rag1-/- mice
Fig. 12B
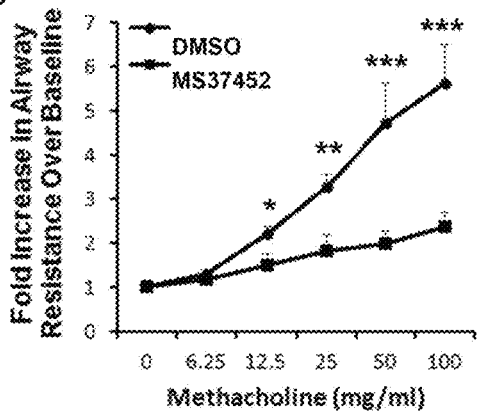
Fig. 12C
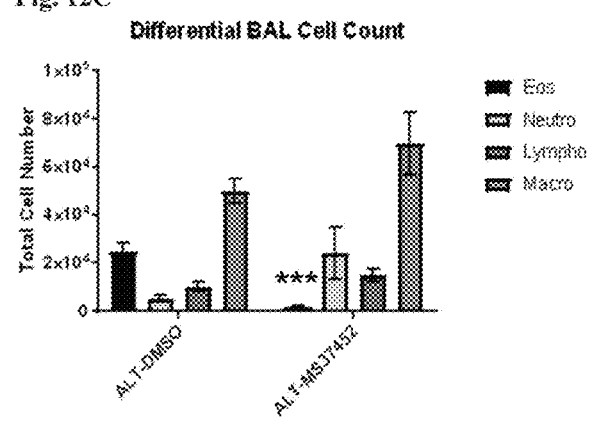
Fig. 12D  Alt+DMSO    Alt+MS37452
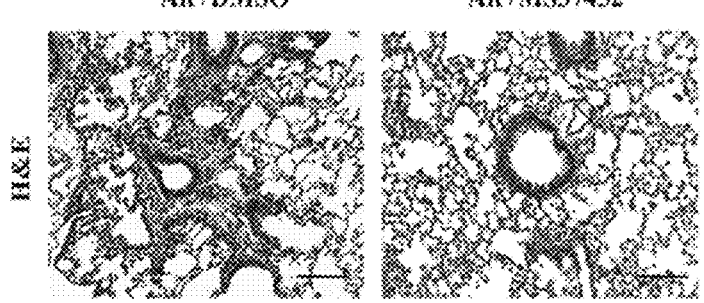

METHODS OF TREATING STEROID RESISTANT DISEASES AND CONDITIONS

CROSS-REFERENCE TO RELATED APPLICATIONS

This application claims the benefit of priority under 35 U.S.C. § 119(e) to U.S. Provisional Patent Application No. 62/620,582, filed Jan. 23, 2018. The entire disclosure of U.S. Provisional Patent Application No. 62/620,582 is incorporated herein by reference.

GOVERNMENT SUPPORT

This invention was made with government support under grant numbers R01 HL126895, and R01 AI102943, and 5R01 AI137970-02 received from the National Institutes of Health. The government has certain rights in the invention.

BACKGROUND

Steroids are frequently used in inflammatory and allergic diseases. These are the most potent anti-inflammatory medications available in clinical practice. Most patients are able to use this family of medication on a chronic basis. A small fraction of these patients develops steroid resistance over time. Steroids are also the mainstay of therapy in asthma. About 20% of asthmatic patients receiving chronic steroid therapy develop steroid resistance and become refractory to treatment (Martin R J et al. National Heart, Lung, and Blood Institute's Asthma Clinical Research Center. The Predicting Response to Inhaled Corticosteroid Efficacy (PRICE) trial. J Allergy Clin Immunol. 2007; 119(1):73-80; Adcock I M et al. Steroid resistance in asthma: mechanisms and treatment options. Curr Allergy Asthma Rep. 2008; 8(2)). Consequently, they experience severe and uncontrolled asthma and account for 60% of the total cost for asthma (Ivanova J I et al. Effect of asthma exacerbations on health care costs among asthmatic patients with moderate and severe persistent asthma. J Allergy Clin Immunol. 2012; 129(5):1229-35). Some of these severe and poorly controlled patients benefit from biologics such as Omalizumab, Mepolizumab or Reslizumab. However, many patients do not respond to these biologics (Wenzel S E. Asthma phenotypes: the evolution from clinical to molecular approaches. Nat Med. 2012; 18(5):716-25; Levy B D et al. Future Research Directions in Asthma: An NHLBI Working Group Report. Am J Respir Crit Care Med. 2015; 192(11):1366-72; Kelly E A et al. Mepolizumab Attenuates Airway Eosinophil Numbers, but Not Their Functional Phenotype, in Asthma. Am J Respir Crit Care Med. 2017; 196:1385-1395). Hence there is an unmet need for new therapeutic agents that benefit steroid resistant asthma.

Although the exact mechanism of steroid resistance is still poorly understood, it is commonly believed that inflammatory cells become steroid resistant over time. Asthma is driven by a type 2 immune response (Woodruff P G et al. T-helper type 2-driven inflammation defines major subphenotypes of asthma. Am J Respir Crit Care Med. 2009; 180:388-95). The major type 2 immune response cells are type 2 T helper cells (Th2), type 2 innate lymphoid cells (IL2s) and their downstream effector cells such as eosinophils, basophils and mast cells. Th2 cells are known to develop steroid resistance in some asthmatic patients (Woodruff P G et al. T-helper type 2-driven inflammation defines major subphenotypes of asthma. Am J Respir Crit Care Med. 2009; 180:388-95. PMCID: PMC2742757). Type 2 innate lymphoid cells (ILC2s) are the latest identified type 2 effector cells of asthma (Moro K et al. Innate production of T(H)2 cytokines by adipose tissue-associated c-Kit(+) Sca-1(+) lymphoid cells. Nature. 2010; 463(7280):540-4; Neill D R et al. Nuocytes represent a new innate effector leukocyte that mediates type-2 immunity. Nature. 2010; 464(7293):1367-70; Saenz S A et al. IL25 elicits a multipotent progenitor cell population that promotes T(H)2 cytokine responses. Nature. 2010; 464(7293):1362-6.; Mjosberg J M et al. Human IL-25- and IL-33-responsive type 2 innate lymphoid cells are defined by expression of CRTH2 and CD161. Nature Immunol. 2011; 12(11):1055-1062; Christianson C A et al. Persistence of asthma requires multiple feedback circuits involving type 2 innate lymphoid cells and IL-33. J Allergy Clin Immunol. 2015; 136(1):59-68). There is only one publication in the literature that addressed steroid resistance of ILC2s in mice (Kabata H et al. Thymic stromal lymphopoietin induces corticosteroid resistance in natural helper cells during airway inflammation. Nat Commun. 2013; 4:2675). Steroid resistance of ILC2s in human asthma is unknown. Characterization of human ILC2s have primarily been done with blood innate lymphoid cells (ILCs). Although blood studies are important as biomarkers, blood cells do not always accurately reflect airway cells (Liu S et al. Steroid Resistance of Airway Type 2 Innate Lymphoid Cells (ILC2s) from Severe Asthma: The Role of Thymic Stromal cell Lymphopoietin (TSLP). J Allergy Clin Immunol. 2017; pii: S0091-6749(17)30660-7.). For this reason it is important to examine steroid response of airway ILC2s in asthma and related inflammatory lung diseases.

BRIEF DESCRIPTION OF THE DRAWINGS

FIGS. 1A and 1B show the effect of dexamethasone (Dex) on blood (A) and bronchoalveolar lavage (BAL) (B) Type 2 innate lymphoid cells (ILC2s). Peripheral blood mononuclear cells (PBMC) and BAL cells from an asthmatic patient were cultured with vehicle (V, ethanol)) or dexamethasone (Dex $10^{-7}$M), a synthetic steroid, for 3 days. The frequency of lin–CRTH2+IL7Rα+IL5+ cells (considered as markers of ILC2s) was measured by flow cytometry (FCM) and analyzed by FlowJo. Frequency of dead cells (measured by e-Fluor 780, e-Bioscience) was less than 10% and excluded from the gating. The difference in dead cells between V and Dex was less than 10%). Prostaglandin D2 receptor 2 (CRTH2); interleukin-7 receptor alpha (IL7Rα); interleukin-5 (IL-5).

FIGS. 1C and 1D show the cumulative data on the effect of dexamethasone (Dex) on blood (FIG. 1C) and BAL (FIG. 1D) lin–CRTH2+IL7Rα+IL5+ cells from 14 allergic asthmatic patients.

FIG. 2A shows the effect of cytokines on development of steroid resistance. PBMCs from allergic asthmatic patients were cultured with a combination of ILC2-stimulating cytokines in the presence or absence of Dex for 5 days. The cells were then stained for FCM and gated for IL5+ ILC2s as described under FIG. 1A. *P<0.05 (n=6).

FIG. 2B shows the kinetics of development of resistance against inhibition of IL5+ ILC2s by Dex. PBMCs were cultured with IL2/TSLP (thymic stromal lymphopoietin) plus vehicle or Dex for 1, 3 and 5 days and then analyzed for IL5+ ILC2s by FCM. *P<0.05 (n=4).

FIGS. 2C and 2D show lineage-negative (Lin–) cells ($0.4 \times 10^6$ per culture) from peripheral blood obtained from 3 allergic rhinitis (non-asthmatic) patients were cultured with IL2/IL33 or IL2/TSLP with and without Dex (10-7 M) for 5 days. Cell-free supernatant was analyzed for IL5 by ELISA. Cells were analyzed by FCM for intracellular IL5. Dex inhibition of IL5 secretion and intracellular IL5 expression are presented in FIGS. 1C and 1D respectively. P value for data on panel C was calculated by paired t test due to low N. Interleukin-2 (IL-2); interleukin-33 (IL-33).

FIG. 2E shows the comparison of the effect of Dex on IL5+ ILCs (lin−CRTH2+IL7Rα+) and IL5+ lineage+ cells in BAL. BAL cells were cultured with vehicle or Dex for 5 days, stained and first gated for CD45+ cells and then for lin−, CRTH2+, IL7Rα+, IL5+ cells (IL5+ ILCs) and lin+ IL5+ cells. Each data point is an individual asthma patient (n=9).

FIGS. 3A-3C show the effect of Dex ($10^{-7}$M) on the number of CRTH2+, IL7Rα+, CD25+, TSLPR+, ST2+, and IL25R+ ILCs after culture of PBMCs for 5 days. FIGS. 3A and 3B: Each symbol is an asthmatic patient (N=13). FIG. 3C Effect of Dex ($10^{-7}$M) on expression of growth receptors on ILC2s after culture of PBMCs for 3 days. N=5, *P<0.05. Thymic stromal lymphopoietin protein receptor (TSLPR); interleukin-25 receptor (IL25R).

FIG. 3D: shows the results when PBMCs were cultured with vehicle (V) or Dex ($10^{-7}$M) for 3 days and then incubated with IL2/TSLP (10 ng/ml each) for the indicated time period. pSTAT5+ lin−CRTH2+IL7Rα+ cells were measured by FCM (*P<0.05, N=4). Signal transducer and activator for transcription 5 (STAT5).

FIG. 3E shows the results when PBMCs were cultured with vehicle (V) or Dex ($10^{-7}$M) for 3 days and then incubated with increasing doses of TSLP in the presence of a suboptimal 2 ng/ml dose of IL2 for 3 days. IL5+ lin− CRTH2+IL7Rα+ cells were measured by FCM (*P<0.05, N=3).

FIGS. 4A and 4B show the effect of Dex on cytokine-induced MEK1 (MEK) induction. PBMCs from an asthmatic patient were cultured with medium or IL2 plus one of the two epithelial ILC-inducing cytokines—IL33 and TSLP with and without Dex for 5 days. The expression of MEK on gated live lin−CRTH2+ cells was analyzed by FCM. Representative flow cytograms are shown in FIG. 4A and cumulative data from 7 asthmatic patients is shown in FIG. 4B.

FIGS. 5A-5C show the comparison of induction of top steroid resistant genes by TSLP vs. IL33 in presence of Dex. Sorted Lin−CD45+CD25+ cells from the human lung mononuclear cell population were cultured with vehicle (not shown), IL2/IL33 (33) or IL2/TSLP (T) (10 ng/ml each) with and without Dex (D) ($10^{-7}$M) for 3 days. The expression mRNA for top 8 steroid resistant genes was assayed by real-time PCR. The data is expressed in reference to 18S RNA (N=4, *P<0.05).

FIG. 10B: CBX7 was immunoprecipitated as above and western blotted with an anti-P-300 and anti-acetylated lysine antibody.

FIG. 11A shows western blot for CBX7 following transfection of cells. FIGS. 11B and 11C: Transfected cells were stimulated with anti-CD3/CD28 antibodies for 5 days. The expression of IL4 by GFP+ cells were analyzed by flow cytometry. FIG. 11B shows flow cytogram from a single experiment. FIG. 11C shows data from 4 separate experiments performed with all three ShRNA for CBX7. *: P<0.05 (t test).

FIGS. 12A-12D shows the effect of CBX7 inhibition on features of asthma in a mouse model. Rag1$^{-/-}$ mice (lack T and B cells but have ILCs) were given intranasally the CBX7 inhibitor MS37452 (319 μg/dose equivalent to 500 mM in the tissue) or the vehicle (DMSO) along with the *Alternaria Alternata* allergen extract (10 μg/dose) for 5 consecutive days (N=5 per group). The mice were examined for airway hyperreactivity to methacholine (by Flexivent) and airway inflammation 2 days later. FIG. 12A shows a timeline for the study design. FIG. 12B shows airway hyperreactivity as measured by fold change in airway resistance in response to inhaled methacholine. FIG. 12C shows differential cell count of bronchoalveolar lavage (BAL) from the mice. FIG. 12D shows airway inflammation as demonstrated by H&E staining of the lung tissue from the mice. FIG. 12B, *: P=0.01; : P=0.001; *: P=0.0001, t test; FIGS. 12C and D, ***: P=0.0001, t test.

SUMMARY OF THE INVENTION

Figure 6A:
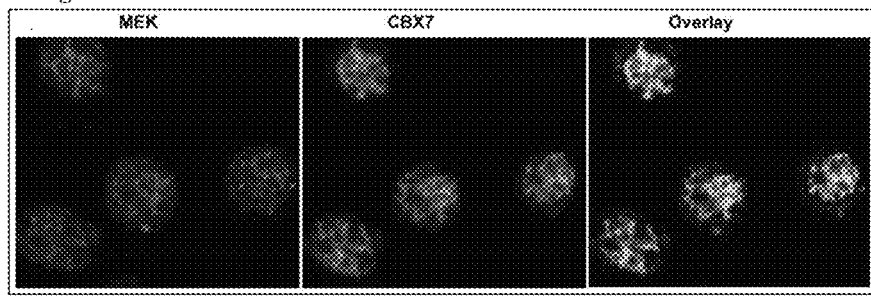
FIG. 6A shows the double immuno-fluorescence staining of CBX7, MEK2 and nuclear staining with DAPI of IL2/TSLP-activated blood ILCs from an asthmatic patient. The overlay confocal image (20×) shows co-localization in the nucleus (N=3). Chromobox homolog 7 (CBX7).

One embodiment of the invention relates to a method treat a subject having a steroid resistant disease or condition comprising administering to the subject a compound that decreases chromobox homolog 7 (CBX7) activity.

One embodiment of the invention relates to a method to treat a subject having a steroid resistant disease or condition comprising administering to the subject a compound that decreases mitogen-activated protein kinase 2 (MEK2) activity.

One embodiment of the invention relates to a method to identify a subject having a steroid resistant disease or condition comprising detecting the expression of CBX7 or MEK2 in a biological sample from the subject, wherein increased expression of CBX7 or MEK2 compared to a control identifies the subject as having steroid resistant disease or condition.

Another embodiment of the invention relates to a method for identifying and treating a subject having a steroid resistant disease or condition comprising (a) obtaining a biological sample from the subject; (b) determining the expression level of CBX7 or MEK2 in the sample; (c) identifying the subject as having a steroid resistant disease or condition if the CBX7 or MEK2 level from the sample is elevated as compared to a control CBX7 or MEK2 level; and (e) administering a compound that decreases CBX7 activity to the identified subject.

Another embodiment of the invention relates to a method to determine the response of a subject to steroid treatment, who has, or is at risk of developing an inflammatory disease resistant to steroid treatment, comprising (a) obtaining a biological sample from the subject; and (b) determining the expression level of CBX7 or MEK2 in the sample; wherein an increase in CBX7 or MEK2 expression in the sample as compared to a control CBX7 or MEK2 expression level determines that the subject is resistant to steroid treatment.

In one aspect of any of the embodiments related to a method, the compound that decreases CBX7 activity is a CBX7 inhibitor. In one aspect, the CBX7 inhibitor is selected from the group consisting of a small-molecule inhibitor, a chemical inhibitor, and antibody, a CBX7 siRNA and combinations thereof. In still another aspect, the CBX7 inhibitor is MS37452 or UNC3866.

In one aspect of any of the embodiments related to a method, the compound that decreases MEK2 activity is a MEK2 inhibitor. In one aspect, the MEK2 inhibitor is selected from the group consisting of a small-molecule inhibitor, a chemical inhibitor, and antibody, a MEK2 siRNA and combinations thereof. In still another aspect, the MEK2 inhibitor is selected from the group consisting of Trametinib, Selumetinib, Pimasertib, Binimetinib, and Cobimetinib.

In one aspect of any of the embodiments related to a method, the steroid resistant disease or condition is an inflammatory disease selected from the group consisting of asthma, an inflammatory lung disease, allergic rhinitis, and sinusitis. In one aspect, the inflammatory lung disease is associated with a chronic obstructive disease of the airways. In yet another aspect, the inflammatory lung disease is associated with viral induced inflammation. In still another aspect, the inflammatory lung disease is triggered by the subject's exposure to environmental conditions including second hand smoke, primary tobacco smoke, and/or an allergen. In yet another aspect, the inflammatory disease is asthma.

In one aspect of any of the embodiments related to a method, the step of administering is by an administration route selected from the group consisting of injection, oral, inhalation and topical.

In one aspect of any of the embodiments related to a method, the biological sample is selected from the group consisting of serum, plasma, blood, sputum, peripheral blood mononuclear cells (PBMCs), epithelial cells, sinus tissue, nasal tissue, and lung tissue.

In any of the embodiments of the invention, the subject is a human.

DETAILED DESCRIPTION OF THE INVENTION

The present invention generally relates to novel methods for predicting, identifying and/or treating subjects having a steroid resistant disease or condition. The invention includes the determining the expression of Chromobox homolog 7 (CBX7) and/or mitogen-activated protein kinase 2 (MEK2) in a biological sample from the subject.

As disclosed herein, CBX7 interacts with MEK2, the transcriptional co-activators casein kinase 2 alpha (CK2α) and P-300 and the RNA polymerase Pol-II. Inhibition of CBX7 pharmacologically (with MS37452 as an example of an inhibitor) and genetically (shRNA-mediated knockdown and germline deletion of the CBX7 gene) resulted in reduced expression of type 2 cytokines (interleukine-4 (IL4), interleukin-5 (IL5) and interleukin-13 (IL13)) and their master transcription factor GATA3 in vitro and in vivo. Consequently, CBX7 inhibition resulted in significantly attenuated asthma. Type 2 cytokine genes are epigenetically bivalent and marked with H3K4me3, H3K27me3 and H3K27ac. CBX7 directly binds the type 2 cytokine genes. Inhibition of MEK2 and CBX7 blocks the binding of CBX7 to the cytokine genes. The inventor believes that MEK2 most likely phosphorylates CBX7, allowing its DNA binding and recruitment of transcriptional activators (CK2a, P-300, and Pol-II). The assembly of this multimolecular protein complex at the promoter site results in type 2 cytokine gene transcription.

CBX7 is a chromobox domain-containing protein that belongs to the polycomb repressor complex 1 (PRC1) (Aloia L et al. Polycomb complexes in stem cells and embryonic development. Development. 2013; 140(12):2525-34; Gao Z et al. PCGF homologs, CBX proteins, and RYBP define functionally distinct PRC1 family complexes. Mol Cell. 2012; 45(3):344-56; Klauke K et al. Polycomb Cbx family members mediate the balance between haematopoietic stem cell self-renewal and differentiation. Nat Cell Biol. 2013; 15(4):353-62). Other members of this PRC1 complex include polycomb group RING finger 3/5 (PCGF3/5), ring finger protein 1 (RING1B), B lymphoma Mo-MLV insertion region 1 homolog (BMI1), polycomb group ring finger 2 (Mel-18) and casein kinase 2 (CK2). The association of CBX7 with Mel-18 and BMI1 is of particular interest. Knockout studies have shown that Mel-18 is essential for GATA3 transcription and Th2 differentiation (Kimura M et al. Regulation of Th2 cell differentiation by mel-18, a mammalian polycomb group gene. Immunity. 2001; 15(2): 275-87), whereas BMI1 is important for GATA binding protein 3 (GATA3) stability and type 2 cytokine expression (Hosokawa H et al. Regulation of Th2 cell development by Polycomb group gene bmi-1 through the stabilization of GATA3. J Immunol. 2006; 177(11):7656-64; Yamashita M et al. Bmi1 regulates memory CD4 T cell survival via repression of the Noxa gene. J Exp Med. 2008; 205(5):1109-20). BMI1−/− mice are unable to mount allergic/eosinophilic airway inflammation (Yamashita M et al. Bmi1 regulates memory CD4 T cell survival via repression of the Noxa gene. J Exp Med. 2008; 205(5):1109-20). MEK/ERK phosphorylates CBX7 at T118, which stabilizes its interaction with Mel-18 and BMI1 (Wu H A et al. Mitogen-activated protein kinase signaling mediates phosphorylation of polycomb ortholog Cbx7. J Biol Chem. 2013; 288(51):36398-408). Thus, CBX7 and MEK2 could jointly promote type 2 cytokine production through recruitment of Mel-18 and BMI1 under the protagonistic milieu of thymic stromal lymphopoietin (TSLP) and dexamethasone (Dex). CBX7 directly upregulates positive regulators of lymphoid cells: Fos, FosB, Egr1, and TRIM24 (Pallante P et al. CBX7 modulates the expression of genes critical for cancer progression. PLoS One. 2014; 9(5):e98295). CBX7 downregulates GR effectors—HDAC2, annexin A1, and protein phosphatase 2A.

The present invention provides for a method to treat a subject having a steroid resistant disease or condition comprising administering to the subject a compound that decreases CBX7 activity or decreases the activity of MEK2.

The present invention also provides for a method for to identify a subject having a steroid resistant disease or condition. The method comprises detecting the expression of CBX7 in a biological sample from the subject, wherein increased expression of CBX7 compared to a control level of CBX7 identifies the subject as having steroid resistant disease or condition. The method further comprises treating the subject identified as having a steroid resistant disease or condition by administering a compound that decreases CBX7 activity.

The present invention further provides for a method for identifying and treating a subject having a steroid resistant disease or condition. The method comprising obtaining a biological sample from the subject; determining the expression level of CBX7 in the sample; identifying the subject as having a steroid resistant disease or condition if the CBX7 level from the sample is elevated as compared to a control CBX7 level; and administering a compound that decreases CBX7 activity to the identified subject.

The present invention further provides for a method to predict the response of a subject to steroid treatment, who has, or is at risk of developing an inflammatory disease resistant to steroid treatment. The method comprises obtaining a biological sample from the subject; and determining the expression level of CBX7 in the sample; wherein an increase in CBX7 expression in the sample as compared to a control CBX7 level predicts the subject to be resistant to steroid treatment.

The present invention also provides for a method to identify a subject having a steroid resistant disease or condition. The method comprises detecting the expression of mitogen-activated protein kinase 2 (MEK2) in a biological sample from the subject, wherein increased expression of MEK2 compared to a control identifies the subject as having steroid resistant disease or condition.

The present invention further comprises a method for identifying and treating a steroid resistant disease or condition. The method comprises obtaining a biological sample from the subject; determining the expression level of MEK2 in the sample; identifying the subject as having a steroid resistant disease or condition if the MEK2 level from the sample is elevated as compared to a control MEK2 level; and administering a compound that decreases MEK2 activity to the identified subject.

The present invention also provides a method to determine or predict the response of a subject to steroid treatment, who has, or is at risk of developing an inflammatory disease resistant to steroid treatment. The method comprises obtaining a biological sample from the subject; and determining the expression level of MEK2 in the sample; wherein an increase in MEK2 expression in the sample as compared to a control MEK2 level determines that the subject is resistant to steroid treatment.

One embodiment of the invention is a CBX7 inhibitor for use in the treatment of an inflammatory disease resistant to steroid treatment in a subject.

Another embodiment of the invention is a MEK2 inhibitor for use in treating an inflammatory disease resistant to steroid treatment in a subject.

Steroid resistant diseases or conditions can be an inflammatory disease. Such inflammatory diseases can include asthma, inflammatory lung diseases, allergic rhinitis, and sinusitis. Inflammatory lung disease can be associated with a chronic obstructive disease of the airways. Inflammatory lung disease can also be associated with viral induced inflammation. An inflammatory lung disease can be triggered by the subject's exposure to environmental conditions such as second-hand smoke, primary tobacco smoke and one or more allergens. In a preferred embodiment of the invention, the inflammatory disease is asthma.

The term "sample" or "biological sample" can be used generally to refer to a sample of any type which contains products that are to be evaluated by the present methods, including but not limited to, serum, plasma, blood, a sample of isolated cells, a tissue sample and/or a bodily fluid sample. A biological sample can include any bodily fluid or tissue from a subject that may contain the proteins contemplated herein, as well as the RNA and genes that encode the proteins. In some embodiments, the sample may comprise serum, blood, plasma or peripheral blood mononuclear cells (PBMCs), leukocytes, monocytes, lymphocytes, basophils or eosinophils, sinus tissue, nasal tissue or lung tissue. In one aspect, the methods of the present invention can be performed on an ex vivo biological sample.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated (or increased) as compared to a control, downregulated (or decreased) as compared to a control, or unchanged as compared to a control or increased or decreased as compared to a reference or control level. Therefore, the step of detecting or determining expression does not require that expression of the gene actually is upregulated or downregulated or increased or decreased, but rather, can also include detecting or determining that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: mass spectrometry, Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, Anal. Biochem. 212:457; Schuster et al., 1993, Nature 365: 343). Other suitable assays for measuring the binding of one protein to another include, for example, immunoassays such as enzyme linked immunoabsorbent assays (ELISA) and radioimmunoassays (MA); or determination of binding by monitoring the change in the spectroscopic or optical properties of the proteins through fluorescence, UV absorption, circular dichroism, or nuclear magnetic resonance (NMR).

As used herein, reference to a control, means a subject who is a relevant reference or control to the subject being evaluated by the methods of the present invention. The control can be matched in one or more characteristics to the subject. The reference or control expression level used in the comparison of the methods of the present invention can be determined from one or more relevant reference or control subjects.

In one aspect of the invention, an increased expression level of CBX7 and/or MEK2 is determined when the subject's CBX7 and/or MEK2 expression level is at least greater than one standard deviation (also defined as one standard deviation from or beyond the mean) from the mean as compared to the control or reference and/or is determined to be significantly higher (such as statically significantly different).

In still other aspects, the relative expression level of CBX7 and/or MEK2 is at least about 5%, at least about 10%, at least about 20%, at least about 30%, at least about 40%, at least about 50%, at least about 60%, at least about 70%, at least about 80%, or at least about 90%, greater (i.e. increased) from the expression level of the reference/control. In still another aspect, the expression level of CBX7 and/or MEK2 is at least about a 2 fold, at least about a 3 fold, at least about a 4 fold, at least about a 5 fold, at least about a 10-fold, at least about a 20 fold, at least about a 25 fold, at least about a 30 fold, at least about a 40 fold or at least about a 50 fold greater from the expression level of the reference/control.

In one aspect of the invention, the subject identified as having a steroid resistant disease or condition is administered a compound that decreases CBX7 activity. In one aspect, the compound can be CBX7 inhibitor and/or modulator. Such as inhibitor can include a small-molecule inhibitor, a chemical inhibitor, and antibody, a CBX7 siRNA and combinations thereof. Examples of a CBX7 inhibitor are MS37452 and UNC3866.

In yet aspect of the invention, the subject identified as having a steroid resistant disease or condition is administered a compound that decreases MEK2 activity. In one aspect, the compound can be MEK2 inhibitor and/or modulator. Such as inhibitor can include a small-molecule inhibitor, a chemical inhibitor, and antibody, a MEK2 siRNA and combinations thereof. Examples of MEK2 inhibitors are Trametinib, Selumetinib, Pimasertib, Binimetinib, Cobimetinib, PD184352 (CI-1040), Refametinib, U0126-EtOH, and SL327.

In still another aspect of the invention, the compound that decrease CBX7 activity and/or MEK2 activity can be administered to the subject by a method such as injection, oral administration, inhalation or topical administration. Topical administration can include cutaneous application in the form of a lotion, an ointment or a cream.

In any of the aspects of the invention, the subject can be a human.

Another embodiment of the present invention relates to a kit for use in the methods of the invention disclosed herein.

The following examples are provided for illustrative purposes and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

This example shows steroid resistance of airway ILC2s and T cells from asthmatic patients.

Steroid response of ILC2s from the bronchoalveolar lavage (BAL, obtained during bronchoscopy) and blood obtained from asthmatic patients was studied. Blood was processed to isolate mononuclear cells (MNC). BAL cells were studied without further processing. MNC and BAL cells were cultured with dexamethasone (Dex, $10^{-7}$M) or vehicle (ethanol) for 3 days. Interluekin-5 (IL5)-expressing ILC2s were examined by flow cytometry and analyzed by FlowJo. IL5+ ILC2s were identified as Lin−CRTH2+ IL7Rα+ cells (lin: lineage markers included CD3, CD14, CD16, CD19, CD20, CD56 and FcεRI). Frequency of dead cells (measured by e-Fluor 780, e-Bioscience) was less than 10% and excluded from the gating. The difference in dead cells between V and Dex was less than 10%). A representative flow cytogram from the blood and BAL ILC2s are shown in FIGS. 1A & 1B, respectively. FIG. 1A and FIG. 1B show that Dex caused a remarkable inhibition of IL5+ ILC2s from the blood but not BAL. FIG. 1C and FIG. 1D show cumulative data from 14 asthmatic patients. A statistical analysis shows that Dex significantly inhibited blood but not BAL IL5+ILC2s from the asthmatic patients.

Example 2

This example shows the IL7Rα ligands—IL7 and TSLP induce steroid resistance in vitro.

The effect of various combinations of ILC2-stimulating cytokines on induction of steroid resistance in vitro was examined. It was determined that the presence of IL7 and TSLP but not IL25 or IL33 in the cytokine combo was associated with the development of steroid resistance (FIG. 2A). IL7 and TSLP attenuated Dex-inhibition of IL5+ ILC2 in the blood. Note that IL2 was added to all cultures as an ILC growth factor. It did not make any difference for steroid resistance. Kinetics analysis showed that the development of steroid resistance required a prolonged, 5 days of exposure to these cytokines (FIG. 2B). Dex did not significantly change the number of lin− cells in the culture.

The direct effect of Dex on isolated lineage− negative (Lin−) cells (representing ILCs) from the peripheral blood was examined. The effect of Dex was measured by two approaches: measurement of secreted IL5 by ELISA and measurement of the expression of intracellular IL5 by FCM. Dex inhibited IL5 secretion by IL2/IL33-stimulated ILCs by nearly 79% (FIG. 2C). In contrast, it inhibited IL5 secretion by IL2/TSLP-stimulated ILCs by only 25%. The measurement of intracellular IL5 in ILCs from the same experiment showed a similar result. Dex inhibited intracellular IL5 expression in IL2/IL33- and IL2/TSLP-stimulated ILCs by 65% and 18%, respectively (FIG. 2D).

Steroid resistance of IL5+lineage+ cells (which represent T cells, NK cells, myeloid cells and mast cells) in the BAL as examined and compared them with ILC2s. IL5+lineage+ BAL cells from these asthmatic subjects were also steroid resistant (FIG. 2E). However, their steroid resistance was milder when compared to the steroid resistance of ILC2s. Note that the frequency of IL5+lineage+ cells was much higher than that of IL5+ ILC2s in BAL. In some patients Dex actually increased the number of IL5+ ILC2s likely due to the increased number of CRTH2+IL7Rα+ cells.

Example 3

This example shows that Dex upregulates select ILC2 receptors (IL7Rα, TSLPR and CD25) and facilitates sustained STAT5 signaling.

It was observed that Dex inhibited the expression of CRTH2, upregulated IL7Rα (Franchimont D et al. Positive effects of glucocorticoids on T cell function by up-regulation of IL-7 receptor alpha. J Immunol. 2002; 168(5):2212-8), CD25 and TSLPR (FIG. 3A-C) and had negligible effect on ST2 and IL25R. The effect on IL7Rα is in agreement with a microarray data, which showed that IL7Rα was one of the top upregulated genes in Dex-treated lymphocytes (Franchimont D et al. Positive effects of glucocorticoids on T cell function by up-regulation of IL-7 receptor alpha. J Immunol. 2002; 168(5):2212-8). Both IL7 and TSLP utilize IL7Rα, which activates STAT5 signaling. The effect of Dex preincubation on IL2/TSLP induced phospho-STAT5 in ILCs was examined. Preculture with Dex amplified the magnitude and duration of pSTAT5 signaling (FIG. 3D). Dex reduced the threshold for TSLP activation of ILC2s by two-fold (FIG. 3E).

Example 4

This example shows that Dex inhibits interleukin-33 (IL33) but not TSLP-induced MEK1/2.

The inventors have previously reported that MEK1/2, an upstream activator of ERK1/2 MAPK, is upregulated by certain cytokines (Liang Q et al. IL-2 and IL-4 stimulate MEK1 expression and contribute to T cell resistance against suppression by TGF-beta and IL-10 in asthma. J Immunol. 2010; 185(10):5704-13). Heightened MEK1/2 mediates steroid resistance of lymphocytes. The effect of IL33 and TSLP on MEK1/2 induction and the effect of Dex was examined. FIG. 4A shows that both IL33 and TSLP upregulated MEK1/2 in ILC2s. Dex inhibited IL33-induced MEK1/2 but failed to inhibit TSLP-induced MEK1/2.

Example 5

This example shows that Glucocorticoid Receptor (GR) protagonizes TSLP to induce high levels of select steroid resistant genes.

MEK1 translocates to the nucleus and binds to the promoter of c-Fos, a component of AP1, which antagonizes the transrepression activity of GR (Guo L et al. Nuclear translocation of MEK1 triggers a complex T cell response through the corepressor silencing mediator of retinoid and thyroid hormone receptor. J Immunol. 2013; 190(1):159-67). The inventors and others have reported that MEK1 binds to the co-repressor SMRT (NCOR2) and causes its nuclear export (Guo L et al. Nuclear translocation of MEK1 triggers a complex T cell response through the corepressor silencing mediator of retinoid and thyroid hormone receptor. J Immunol. 2013; 190(1):159-67; Hong S H et al. The SMRT corepressor is regulated by a MEK-1 kinase pathway: inhibition of corepressor function is associated with SMRT phosphorylation and nuclear export. Mol Cell Biol. 2000; 20(17):6612-25). GR utilizes SMRT to recruit histone deacetylase (HDAC) (Wang D et al. Corepressor binding to progesterone and glucocorticoid receptors involves the activation function-1 domain and is inhibited by molybdate. Mol Endocrinol. 2005; 19(6):1483-500; Ki S H et al. Glucocorticoid receptor (GR)-associated SMRT binding to C/EBPbeta TAD and Nrf2 Neh4/5: role of SMRT recruited to GR in GSTA2 gene repression. Mol Cell Biol. 2005; 25(10):4150-65; Ronacher K et al. Ligand-selective transactivation and transrepression via the glucocorticoid receptor: role of cofactor interaction. Mol Cell Endocrinol. 2009; 299(2):219-31). HDAC-mediated histone deacetylation of chromatin is one mechanism by which GR executes transrepression. Thus, MEK-SMRT interaction leads to impaired GR transrepression. The importance of MEK in steroid resistance was recently confirmed in a functional genomics study of leukemic cells (Jones C L et al. MAPK signaling cascades mediate distinct glucocorticoid resistance mechanisms in pediatric leukemia. Blood. 2015; 126(19):2202-12). Using a genome-wide gene knockdown approach this study identified over 50 genes that induced steroid resistance. Two MEK isoforms (MEK2 & MEK4) were the top steroid resistant genes. Top 10 steroid resistant genes in ILC2s induced by TSLP and IL33 with and without Dex was examined. Two of these genes (TAT, MAP2K4/MEK4) were detected at low levels (PCR Ct>28) and were not analyzed. Three broad patterns of expression (FIGS. 5A&B) were observed: 1) Four genes—AKT3, ARID5, ICT1 and SES2 were steroid sensitive regardless of stimulation with IL33 or TSLP. 2) Three genes—CBX7, MAP2K2 (MEK2) and TLR2 were steroid resistant for both stimulants. Remarkably, Dex not only failed to antagonize but actually protagonized the induction of CBX7, MAP2K2 and TLR2 by TSLP. 3) TNFRSF19 expression by IL33 was antagonized but that by TSLP was protagonized by Dex. Based upon these results it was concluded that CBX7, MEK2 and TLR2 were strong candidates for steroid resistant genes.

Example 6

This example shows that CBX7 and other protein regulator of cytokinesis 1 (PRC1) members interact with MEK2 and GR.

Its induction by IL33 and TSLP suggests that CBX7 interacts with proteins involved in regulation of cytokine production. The interaction of MEK2 and CBX7 was examined. Double immunofluorescence staining and confocal microscopy showed that a significant amount of MEK2 localized to the nucleus and interacted with CBX7 (FIG. 6A and discussed in Example 9). Co-precipitation studies demonstrated that CBX7 formed a multimolecular complex with MEK2, GR, and Mel-18 (FIG. 6B) in IL2/TSLP-stimulated blood CD4 T cells. The results establish a new paradigm, where MEK2 interacts with CBX7, Mel-18, and GR in the nucleus and influences their function.

Example 7

This example shows that Chronic allergen exposure and TSLP induce the steroid resistant gene CBX7.

Figure 7A:
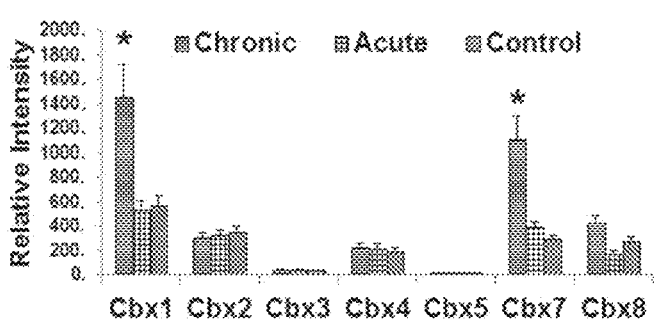
FIGS. 7A and 7B: shows the expression of mRNA for CBX family proteins (CBX1-7) and MEK1-4 in the mouse lung from chronic and acute asthma and saline controls (N=6 mice/group, *P<0.05).
Figure 7B:
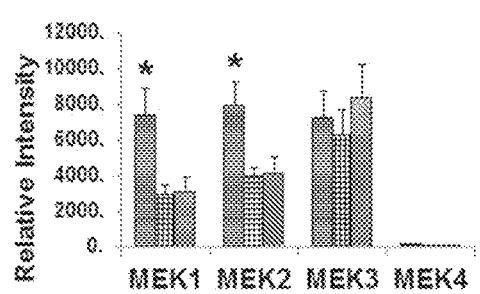
Figure 7C:
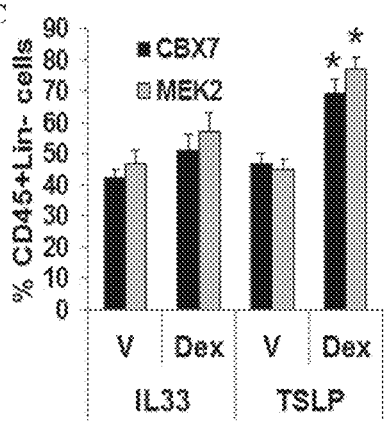
FIG. 7C: shows the effect of TSLP and IL33+/− Dex on MEK2+& CBX7+ lung ILCs as quantified by FCM (N=4, *P=0.04).
Figure 7D:
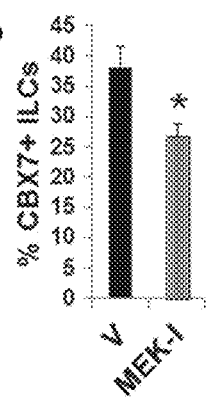
FIG. 7D shows the effect of the MEK inhibitor Trametinib (MEK-I) on CBX7+ ILCs (N=3, P<0.05).

A mouse model of chronic asthma was established by intranasal exposure for 8 weeks to a combination of allergens representing 3 allergen families—indoor allergens (dust mite), mold (*Aspergillus*) and weed (ragweed) (Goplen N et al. Combined sensitization of mice to extracts of dust mite, ragweed, and *Aspergillus* species breaks through tolerance and establishes chronic features of asthma. J Allergy Clin Immunol. 2009; 123(4):925-32.e11). This model of chronic asthma manifests steroid resistance (Duechs M J et al. Development of a novel severe triple allergen asthma model in mice which is resistant to dexamethasone and partially resistant to TLR7 and TLR9 agonist treatment. PLoS One. 2014; 9(3):e91223). The transcriptomic profile of the lung tissue from this chronic asthma model was compared with that from the acute asthma model (standard model with ragweed in alum s.c. sensitization) and saline controls by microarray. CBX1, CBX7, MEK1/2 were selectively upregulated in the chronic model (FIGS. 7A&B) underscoring the importance of chronic stimulation. The induction of MEK2 and CBX7 proteins in human ILCs following treatment was compared with TSLP and IL33+/− Dex for 5 days by FCM. Dex did not affect IL33 but augmented TSLP induction of MEK2 and CBX7 (FIG. 7C), supporting its protagonistic effect at the protein level. MEK-ERK signaling leads to phosphorylation of CBX7 and its interaction with other PRC1 components (Wu H A et al. Mitogen-activated protein kinase signaling mediates phosphorylation of polycomb ortholog Cbx7. J Biol Chem. 2013; 288(51):36398-408). The role of MEK2 in CBX7 regulation was examined. The MEK1/2 inhibitor Trametinib reduced the number of CBX7+ ILCs (FIG. 7D).

Example 8

This example shows that a CBX7 inhibitor blocks inflammatory cytokine production.

Figure 8A:
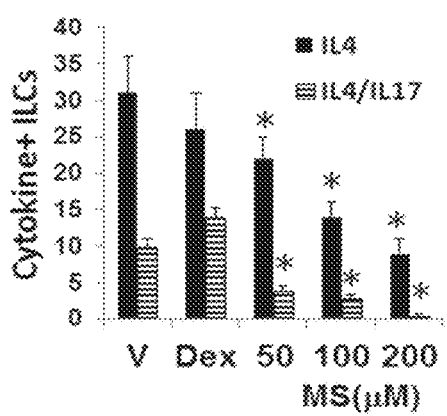
FIG. 8A shows the effect of Dex and the CBX7 inhibitor MS37452 on IL4+ and IL4/IL17+ ILCs. Blood lin− cells were cultured with IL1β/IL2+/− Dex ($10^{-7}$M) or MS for 7 days and IL4+ and IL4/IL17A+ ILCs were measured by FCM (N=4, *P<0.05).
Figure 8B:
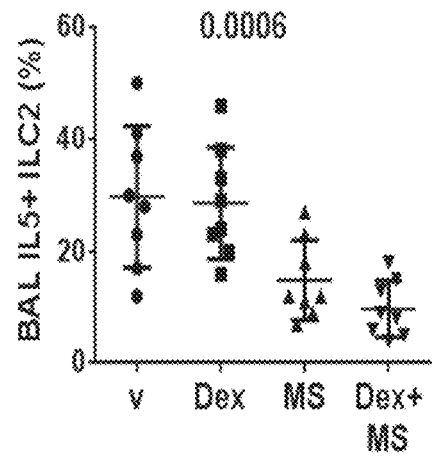
FIG. 8B shows the effect of the CBX7 inhibitor MS37452 (MS) on steroid (Dex) resistant BAL ILC2s. BAL cells were cultured with MS (100 μM) with and without Dex ($10^{-7}$M) for 3 days. IL5 expression by lin−CRTH2+IL7Rα+ ILC2s was measured by FCM (N=8, *: P=0.0006 by Kruskal Walis test).
Figure 8C:
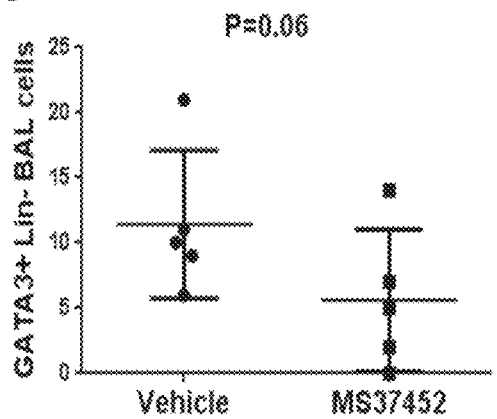
FIGS. 8C and 8D show the effect of the CBX7 inhibitor on GATA3 expression by Lin− BAL cells (FIG. 8C) and IL13 expression by lin+ BAL cells (FIG. 8D). BAL cells from asthmatic patients were cultured with MS (100 μM) or vehicle for 3 days. GATA3 expression by lin− cells and IL13 expression by lin+ cells was measured by FCM (N=5, Mann Whitney U test).
Figure 8D:
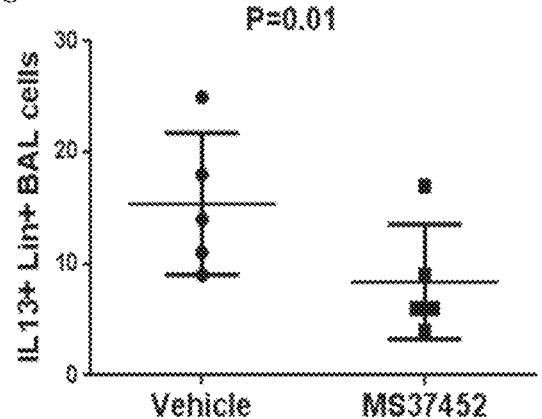

To determine the effect of CBX7, MS37452 was used, which is a CBX7 chromobox-specific inhibitor and does not inhibit other chromobox proteins (Ren C et al. Small-molecule modulators of methyl-lysine binding for the CBX7 chromodomain. Chem Biol. 2015; 22(2):161-8). MS37452 inhibited blood IL4+ ILCs in a dose-dependent manner (FIG. 8A). The inventors have reported that the frequency of Th2/Th17 cells was increased in a subgroup of asthma patients and that Th2/Th17 cells were steroid resistant (Irvin C et al. Increased frequency of dual-positive TH2/TH17 cells in bronchoalveolar lavage fluid characterizes a population of patients with severe asthma. J Allergy Clin Immunol. 2014; 134:1175-1186.e7). It is now shown that there is a dual IL4/IL17A+ subpopulation of ILCs, which is induced by IL1β and IL2. The IL4/IL17A+ ILCs were resistant to Dex but sensitive to MS37452 (FIG. 8A). The inventors have reported that inhibition of MEK1/2 reversed steroid resistance of BAL ILC2s from asthmatic patients (Liu S et al. Steroid Resistance of Airway Type 2 Innate Lymphoid Cells (ILC2s) from Severe Asthma: The Role of Thymic Stromal cell Lymphopoietin (TSLP). J Allergy Clin Immunol. 2017; pii: S0091-6749(17)30660-7). The importance of CBX7 for BAL ILC2 steroid resistance was examined. BAL cells were cultured with MS37452 with and without Dex. Dex failed to inhibit BAL IL5+ILC2s (FIG. 8B). MS37452 (MS) independently inhibited IL5+ ILC2s. The combination of the inhibitor and Dex caused a further inhibition of IL5+ ILC2s and reversed steroid resistance. MS37452 inhibited in ILC2s the expression of GATA3, the master regulator of type 2 cytokines (FIG. 8C). Finally, MS37452 inhibited IL13 expression in lineage+ cells, which mostly represent T cells (FIG. 8D).

Example 9

Figure 6B:
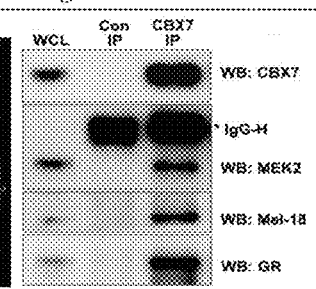
FIG. 6B: shows the co-immunoprecipitation of CBX7 with MEK2, MEL-18 and GR. Blood CD4 T cells ($3 \times 10^6$/sample) were stimulated with IL2/TSLP and Dex for 3 days. Nuclear extract was immunoprecipitated (IP) with an anti-CBX7 or control (Con) IgG ab, western blotted (WB) with anti-CBX7 and reprobed with antibodies against MEK2, Mel-18 and GR. Direct WB with the whole cell lysate (WCL) is also shown (*IgG-H: IgG heavy chain, N=3).
Figure 9:
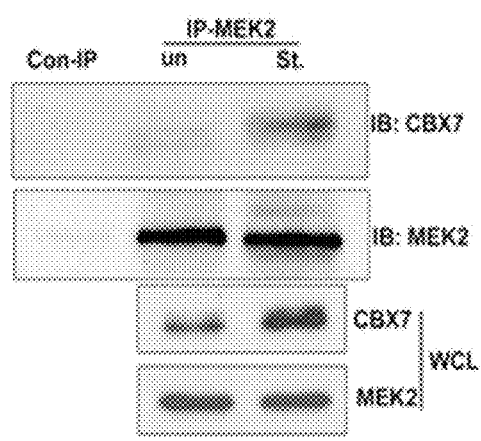
FIG. 9 show CBX7 interaction with MEK2. Immunoblots (IB) with an anti-CBX7 antibody and then re-immunoblotted with an anti-MEK2 antibody is shown. The bottom panel shows immunoblot of the whole cell lysate (WCL) for CBX7 and MEK2. See FIG. 6A for the related confocal microscopy results.

This example shows CBX7 interaction with MEK2. As shown in FIG. 9, isolated peripheral blood mononuclear cells (PBMCs) were stimulated (St.) with plate-bound anti-CD3/anti-CD28 antibodies or left unstimulated (un) for 48 hr. Cells were lysed and immunoprecipitated (IP) with an anti-MEK2 or an isotype control antibody (Con-IP). The immunoprecipiate was first immunoblotted (TB) with an anti-CBX7 and then re-immunoblotted with an anti-MEK2 antibody. The bottom panel shows immunoblot of the whole cell lysate (WCL) for CBX7 and MEK2. The result is representative of 4 experiments. FIG. 6B is related and shows anti-CD3/CD28 antibody stimulated cells (as in FIG. 9) were double immunostained for MEK2 (MEK, red—first panel) and CBX7 (green—middle panel) and analyzed for co-localization (yellow on overlay image—third panel) by confocal microscopy (N=4). Co-precipitation and co-localization studies show that CBX7 and MEK2 physically interact with each other.

Example 10

Figure 10A:
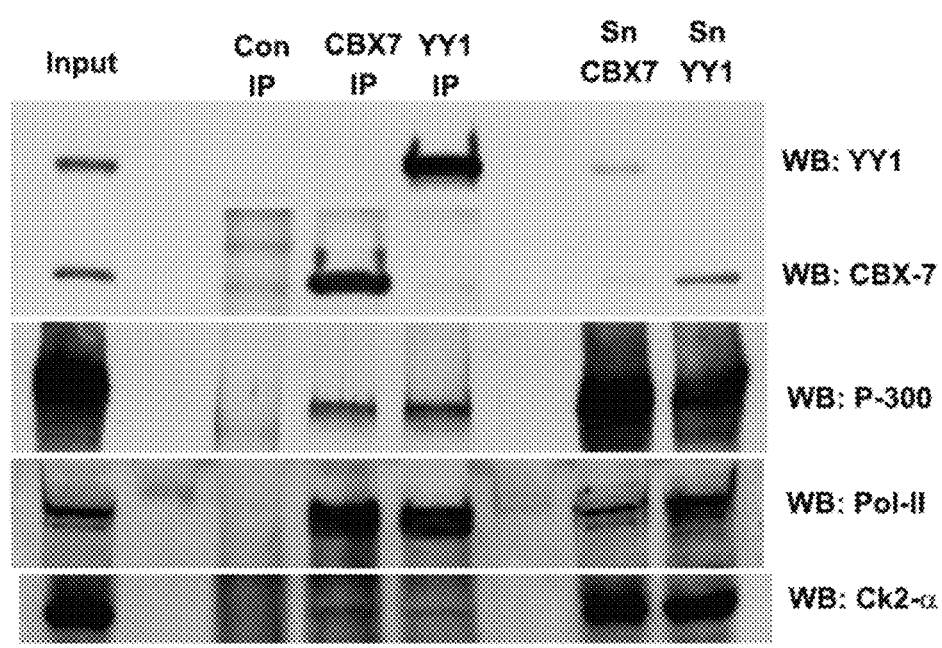
FIGS. 10A and 10B show the interaction of CBX7 with transcriptional activators and regulators. CD4 T cells were stimulated with plate-bound anti-CD3/CD28 antibodies for 48 hrs and then used to immunoprecipitate (IP) with anti-CBX7 and anti-YY1 antibodies or with a control IgG (Con) antibody. The immunoprecipitates, the supernatant (Sn) of the immunoprecipitate and whole cell lysate (input) were sequentially western blotted for YY1 (a regulator of enhancer-promoter loop), CBX7, P-300 (a histone acetyl transferase and transcriptional co-activator), Pol-II (an RNA polymerase), and CK2-a (a recruiter of Pol-II).
Figure 10B:
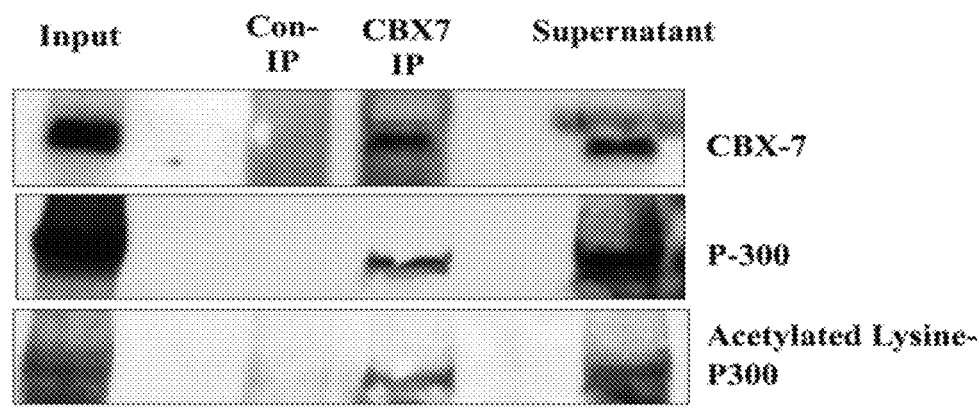

This example shows the interaction of CBX7 with transcriptional activators and regulators. FIG. 10A: CD4 T cells were stimulated with plate-bound anti-CD3/CD28 antibodies for 48 hrs and then used to immunoprecipitate (IP) with anti-CBX7 and anti-YY1 antibodies or with a control IgG (Con) antibody. The immunoprecipitates, the supernatant (Sn) of the immunoprecipitate and whole cell lysate (input) were sequentially western blotted for YY1 (a regulator of enhancer-promoter loop), CBX7, P-300 (a histone acetyl transferase and transcriptional co-activator), Pol-II (an RNA polymerase), and CK2-a (a recruiter of Pol-II). CBX7 did not interact with YY1. However, CBX7 (as well as YY1) interacted with P-300, Pol-II and CK2a. FIG. 10B: In a separate experiment CBX7 was immunoprecipitated as in FIG. 10A and western blotted with an anti-P-300 and anti-acetylated lysine antibody. The latter detected acetylated P-300, which represents the activated form of P-300. The results show that CBX7 directly interacts with transcriptional regulators—P-300 and CK2a as well as Pol-II, the RNA polymerase.

Example 11

Figure 11A:
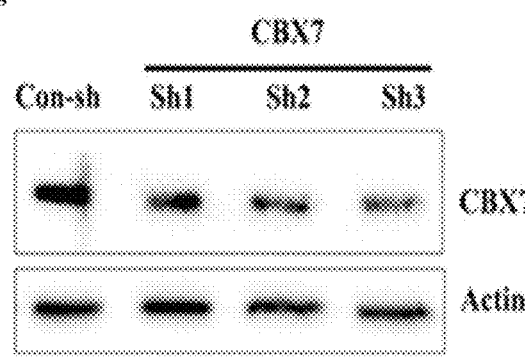
FIGS. 11A-11C show the effect of CBX7 knockdown on IL4 expression by CD4 T cells. CD4 T cells from PBMC were isolated by negative selection using antibody-coated magnetic beads. Cells were transfected with 3 different CBX7-specific shRNA or a scrambled (control) shRNA (con-sh) in a bicistronic GFP-expressing lentiviral vector.
Figure 11C:
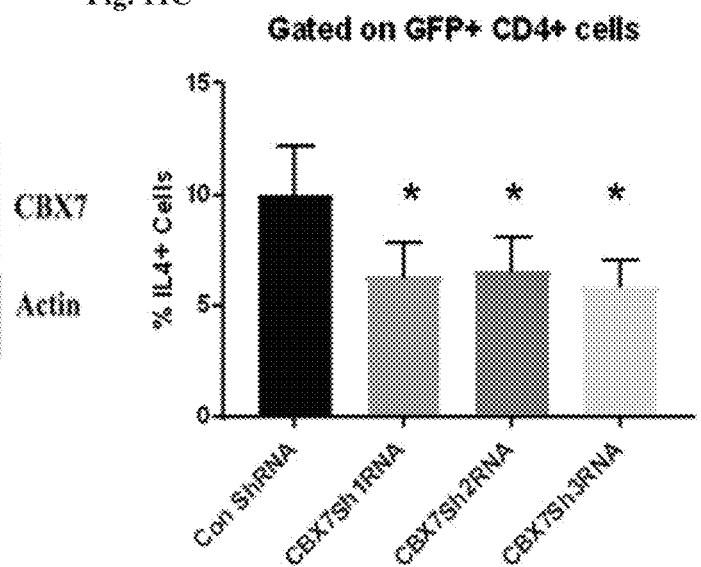
Figure 11B:
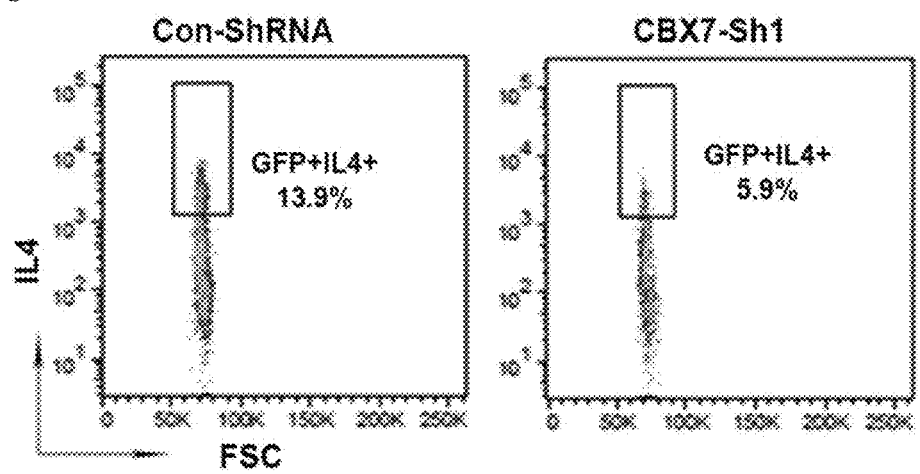

This example shows the effect of CBX7 knockdown on IL4 expression by CD4 T cells. CD4 T cells from PBMC were isolated by negative selection using antibody-coated magnetic beads. Cells were transfected with 3 different CBX7-specific shRNA or a scrambled (control) shRNA (con-sh) in a bicistronic GFP-expressing lentiviral vector. FIG. 11A shows western blot for CBX7 following transfection of cells. The membrane was re-probed for actin to determine equal protein loading. FIGS. 11 and 11C: Transfected cells were stimulated with anti-CD3/CD28 antibodies for 5 days. The expression of IL4 by GFP+ cells were analyzed by flow cytometry. FIG. 11B shows flow cytogram from a single experiment. FIG. 11C shows data from 4 separate experiments performed with all three ShRNA for CBX7. ShRNA-mediated CBX7 knockdown resulted in a significant (*P=0.04, t test) inhibition of IL4 expression by CD4 T cells. The results of ShRNA-mediated knockdown studies show that CBX7 is important for IL4 production by lymphocytes.

Example 12

This example shows the effect of CBX7 inhibition on features of asthma in a mouse model. Rag1$^{-/-}$ mice (lack T and B cells but have ILCs) were given intranasally the CBX7 inhibitor MS37452 (319 µg/dose equivalent to 500 µM in the tissue) or the vehicle (DMSO) along with the *Alternaria Alternata* allergen extract (10 µg/dose) for 5 consecutive days (N=5 per group). The mice were examined for airway hyperreactivity to methacholine (by Flexivent) and airway inflammation 2 days later. FIG. 12A shows a timeline for the study design. FIG. 124B shows airway hyperreactivity as measured by fold change in airway resistance in response to inhaled methacholine. FIG. 12C shows differential cell count of bronchoalveolar lavage (BAL) from the mice. FIG. 4D shows airway inflammation as demonstrated by H&E staining of the lung tissue from the mice. The CBX7 inhibitor MS37452 blocked airway hyperreactivity (FIG. 12B, *: P=0.01; : P=0.001; *: P=0.0001, t test) and eosinophilic inflammation (FIGS. 12C and 12D, ***: P=0.0001, t test) in an ILC-dependent asthma model in mice.

Example 13

Figure 13:
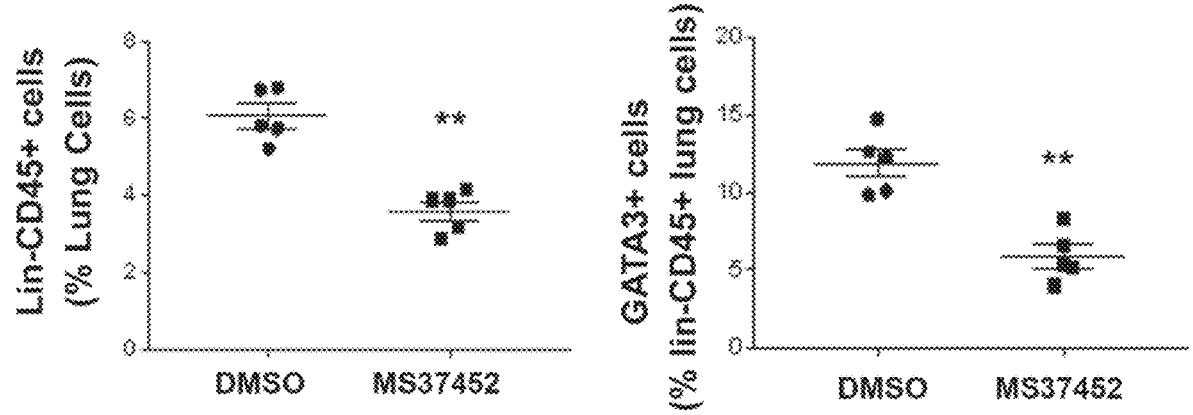
FIG. 13 shows the effect of CBX7 inhibition of lung inflammation in a mouse model. Lung tissue from the asthma model (N=5 per group) (as described in the description of FIGS. 12A-12D) was collagen-digested. The released cells were stained for hematopoietic cells (CD45+) and type 2 immune cells (GATA3+) and analyzed by flow cytometry. (**: P=0.001, t test).

This example shows the effect of CBX7 inhibition of lung inflammation in a mouse model. Lung tissue from the asthma model (N=5 per group) as described under FIG. 13 was collagen-digested. The released cells were stained for hematopoietic cells (CD45+) and type 2 immune cells (GATA3+) and analyzed by flow cytometry. The CBX7 inhibitor MS37452 significantly (**: P=0.001, t test) blocked the influx of inflammatory hematopoietic cells and the expression of GATA3 in lung ILCs in a mouse model of asthma.

Example 14

Figure 14A:
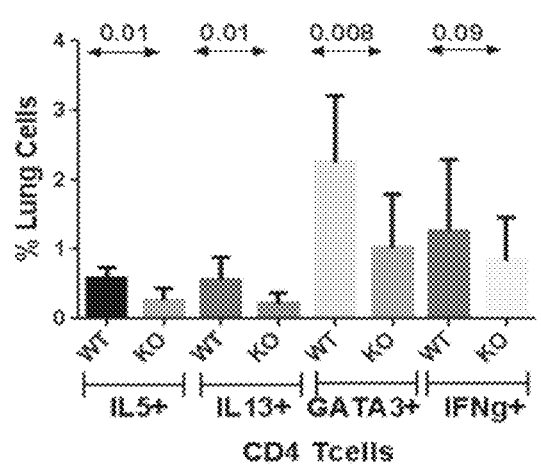
FIGS. 14A and 14B shows the effect of CBX7 knockout on expression of IL5+, IL13+, GATA+ and IFNg+CD4 T cells (FIG. 14A) and ILCs (FIG. 14B) in the airways from mice that were treated with allergens as described in the description of FIGS. 12A-12D. P values [t test] are shown above the graphs.
Figure 14B:
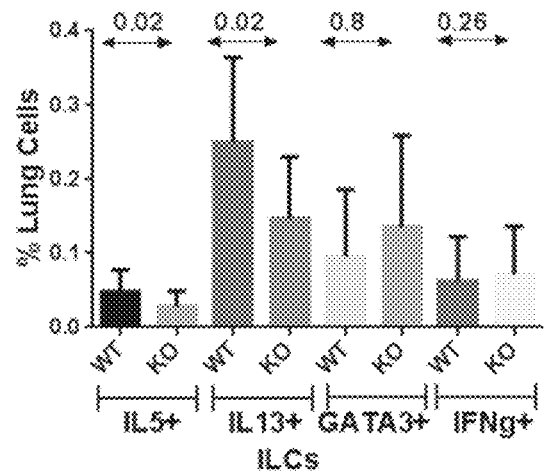

This example shows the effect of CBX7 knockout on type 2 cytokine expression in the airways. CBX7 knockout and wild-type control mice (N=5 per group) were sensitized intranasally to the *Alternaria* allergen extract (10 µg/dose) on 3 alternate days in week 1 and then challenged on 3 consecutive days 3 weeks later. Two days after the last challenge lungs were collagen-digested and the released cells were stained for cytokine and GATA3 positive CD4 T cells (FIG. 6A) and ILCs (lin−CD45+CD25+) cells (FIG. 14B), and analyzed by flow cytometry. CBX7 knockout mice had significantly (P values [t test] are shown above the graphs in FIGS. 14A and 14B) reduced expression of IL5+ and IL13+CD4 T cells and ILCs. CBX7 deletion inhibited GATA3 expression in CD4 T cells but not ILCs. CBX7 gene deletion had no effect on interferon-gamma (IFNg) expression in either cell types. The results from this gene knockout model suggest that CBX7 is essential for expression of type 2 cytokines (IL5 and IL13) and GATA3 in CD4 T cells, and the expression of type 2 cytokines in ILCs.

Example 15

Figure 15A:
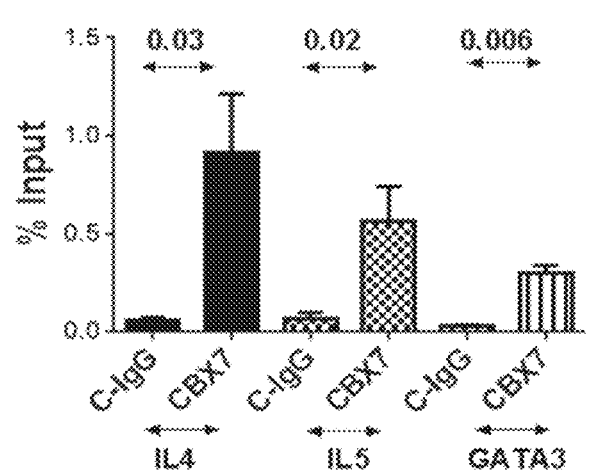
FIGS. 15A-15D show the epigenetic regulation of type 2 genes by CBX7. chromatin immunoprecipitation (ChIP) studies are shown in FIGS. 15A-15D. Details of results are provided in Example 15. P values [t test] are shown above the bar graphs.
Figure 15B:
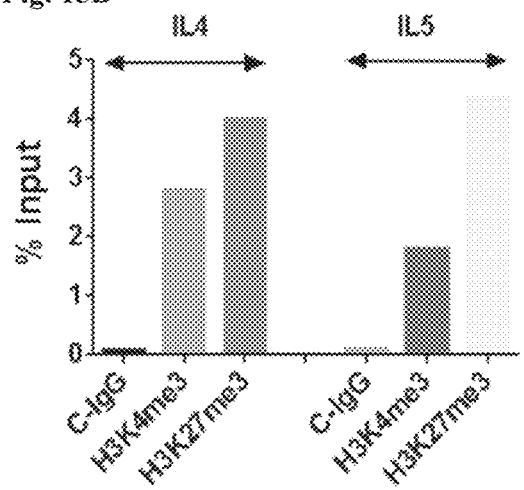
Figure 15C:
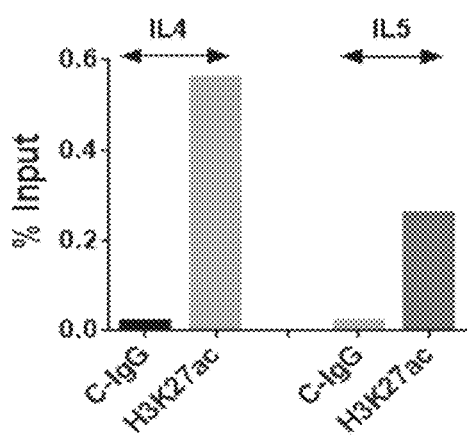
Figure 15D:
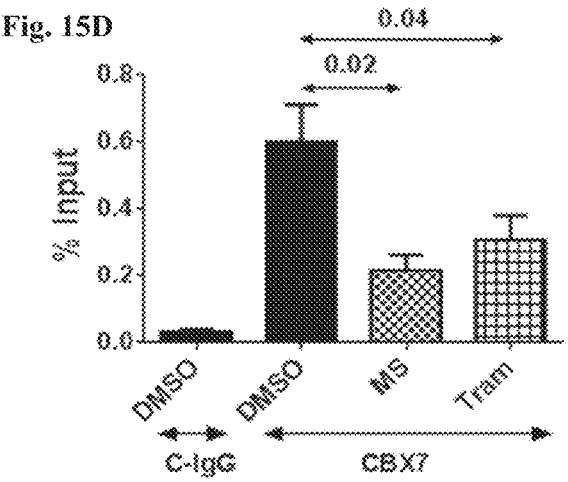

This example shows the genetic and epigenetic regulation of type 2 genes by CBX7. FIG. 15A: Peripheral blood CD4 T cells were isolated, cultured with plate-bound anti-CD3/CD28 antibodies and then used in chromatin immunoprecipitation (ChIP) studies using an anti-CBX7 antibody and an isotype control antibody (C-IgG). PCR was performed on ChIP DNA using primer sets for IL4, IL5 and GATA3 promoter sequences (N=4). CBX7 directly bound to the promoter site of all three genes (P values [t test] are shown above bar graphs). FIG. 15B: ChIP was performed on stimulated CD4 T cells as above using antibodies against the transcriptionally active histone marker H3K4me3, the repressor marker H3K27me3, and a control antibody (C-IgG) (N=1). The IL4 and IL5 gene loci had both types of histone marking—H3K4me3 and H3K27me3. This dual histone marking makes them bivalent genes, which explains how CBX7, which is a H3K27me3 reader, is recruited to a transcriptionally active H3K4me3-marked gene locus. FIG. 15C: CD4 T cells were stimulated as above and then used to perform ChIP with an antibody against the transcriptional enhancer marker H3K27ac, which marks transcriptionally poised genes. The IL4 and IL5 gene loci showed H3K27ac marking, thus demonstrating their transcriptionally poised epigenetic conformation. D: CD4 T cells were stimulated as above in the presence of the CBX7 inhibitor MS37452 (MS, 200 µM) and MEK inhibitor Trametinib (Tram, 10 µM)) and then subjected to ChIP with the anti-CBX7 antibody (N=3). PCR was performed with the ChIP DNA using primers for IL4 promoter. The inhibitors of CBX7 and MEK significantly blocked (P values [t test] are shown above the bar graphs) CBX7 binding to the promoter of IL4 gene.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Martin R J, Szefler S J, King T S, Kraft M, Boushey H A, Chinchilli V M, Craig T J, Dimango E A, Deykin A, Fahy J V, Israel E, Lazarus S C, Lemanske R F Jr, Leone F T, Pesola G R, Peters S P, Sorkness C A, Szwejbka L A, Wechsler M E; National Heart, Lung, and Blood Institute's Asthma Clinical Research Center. The Predicting Response to Inhaled Corticosteroid Efficacy (PRICE) trial. J Allergy Clin Immunol. 2007; 119(1):73-80. PMCID: PMC2872157.
2. Adcock I M, Ford P A, Bhaysar P, Ahmad T, Chung K F. Steroid resistance in asthma: mechanisms and treatment options. Curr Allergy Asthma Rep. 2008; 8(2):171-8. PMID: 18417060.
3. Ivanova J I, Bergman R, Birnbaum H G, Colice G L, Silverman R A, McLaurin K. Effect of asthma exacerbations on health care costs among asthmatic patients with moderate and severe persistent asthma. J Allergy Clin Immunol. 2012; 129(5):1229-35. PMID: 22326484.
4. Wenzel S E. Asthma phenotypes: the evolution from clinical to molecular approaches. Nat Med. 2012; 18(5):716-25. PMID: 22561835.
5. Levy B D, Noel P J, Freemer M M, Cloutier M M, Georas S N, Jarj our NN, Ober C, Woodruff P G, Barnes K C, Bender B G, Camargo C A Jr, Chupp G L, Denlinger L C, Fahy J V, Fitzpatrick A M, Fuhlbrigge A, Gaston B M, Hartert T V, Kolls J K, Lynch SV, Moore W C, Morgan W J, Nadeau K C, Ownby D R, Solway J, Szefler S J, Wenzel S E, Wright R J, Smith R A, Erzurum S C. Future Research Directions in Asthma: An NHLBI Working Group Report. Am J Respir Crit Care Med. 2015; 192(11):1366-72. PMCID: PMC4731702.
6. Kelly E A, Esnault S, Liu L Y, Evans M D, Johansson M W, Mathur S, Mosher D F, Denlinger L C, Jarjour N N. Mepolizumab Attenuates Airway Eosinophil Numbers, but Not Their Functional Phenotype, in Asthma. Am J Respir Crit Care Med. 2017; 196:1385-1395. PMID: 28862877
7. Woodruff P G, Modrek B, Choy D F, Jia G, Abbas A R, Ellwanger A, Koth L L, Arron J R, Fahy J V. T-helper type 2-driven inflammation defines major subphenotypes of asthma. Am J Respir Crit Care Med. 2009; 180:388-95. PMCID: PMC2742757.
8. Moro K, Yamada T, Tanabe M, Takeuchi T, Ikawa T, Kawamoto H, Furusawa J, Ohtani M, Fujii H, Koyasu S. Innate production of T(H)2 cytokines by adipose tissue-associated c-Kit(+)Sca-1(+) lymphoid cells. Nature. 2010; 463(7280):540-4. PMID: 20023630.
9. Neill D R, Wong S H, Bellosi A, Flynn R J, Daly M, Langford T K, Bucks C, Kane C M, Fallon P G, Pannell R, Jolin H E, McKenzie A N. Nuocytes represent a new innate effector leukocyte that mediates type-2 immunity. Nature. 2010; 464(7293):1367-70. PMCID: PMC2862165.
10. Saenz S A, Siracusa M C, Perrigoue J G, Spencer S P, Urban J F Jr, Tocker J E, Budelsky A L, Kleinschek M A, Kastelein R A, Kambayashi T, Bhandoola A, Artis D. IL25 elicits a multipotent progenitor cell population that promotes T(H)2 cytokine responses. Nature. 2010; 464(7293):1362-6. PMCID: PMC2861732.
11. Mjosberg J M, Trifari S, Crellin N K, Peters C P, van Drunen C M, Piet B, Fokkens W J, Cupedo T, Spits H. Human IL-25- and IL-33-responsive type 2 innate lymphoid cells are defined by expression of CRTH2 and CD161. Nature Immunol. 2011; 12(11):1055-1062. PMID: 21909091.
12. Christianson C A, Goplen N P, Zafar I, Irvin C, Good J T Jr, Rollins D R, Gorentla B, Liu W, Gorska M M, Chu H, Martin R J, Alam R. Persistence of asthma requires multiple feedback circuits involving type 2 innate lymphoid cells and IL-33. J Allergy Clin Immunol. 2015; 136(1):59-68. PMCID: PMC4494983.
13. Kabata H, Moro K, Fukunaga K, Suzuki Y, Miyata J, Masaki K, Betsuyaku T, Koyasu S, Asano K. Thymic stromal lymphopoietin induces corticosteroid resistance in natural helper cells during airway inflammation. Nat Commun. 2013; 4:2675. PMID: 24157859.
14. Liu S, Verma M, Michalec L, Liu W, Sripada A, Rollins D, Good J, Ito Y, Chu H, Gorska M M, Martin R J, Alam R. Steroid Resistance of Airway Type 2 Innate Lymphoid Cells (ILC2s) from Severe Asthma: The Role of Thymic Stromal cell Lymphopoietin (TSLP). J Allergy Clin Immunol. 2017; pii: S0091-6749(17)30660-7. PMID: 28433687.
15. Franchimont D, Galon J, Vacchio M S, Fan S, Visconti R, Frucht D M, Geenen V, Chrousos G P, Ashwell J D, O'Shea J J. Positive effects of glucocorticoids on T cell function by up-regulation of IL-7 receptor alpha. J Immunol. 2002; 168(5):2212-8. PMID: 11859107.
16. Liang Q, Guo L, Gogate S, Karim Z, Hanifi A, Leung D Y, Gorska M M, Alam R. IL-2 and IL-4 stimulate MEK1 expression and contribute to T cell resistance against suppression by TGF-beta and IL-10 in asthma. J Immunol. 2010; 185(10):5704-13. PMCID: PMC3367768.
17. Guo L, Chen C, Liang Q, Karim M Z, Gorska M M, Alam R. Nuclear translocation of MEK1 triggers a complex T cell response through the corepressor silencing mediator of retinoid and thyroid hormone receptor. J Immunol. 2013; 190(1):159-67. PMCID: PMC3530839.
18. Hong S H, and Privalsky M L. The SMRT corepressor is regulated by a MEK-1 kinase pathway: inhibition of corepressor function is associated with SMRT phosphorylation and nuclear export. Mol Cell Biol. 2000; 20(17):6612-25. PMCID: PMC86146.
19. Wang D, Simons S S Jr. Corepressor binding to progesterone and glucocorticoid receptors involves the activation function-1 domain and is inhibited by molybdate. Mol Endocrinol. 2005; 19(6):1483-500. PMID: 15774497.
20. Ki S H, Cho I J, Choi D W, Kim S G. Glucocorticoid receptor (GR)-associated SMRT binding to C/EBPbeta TAD and Nrf2 Neh4/5: role of SMRT recruited to GR in GSTA2 gene repression. Mol Cell Biol. 2005; 25(10):4150-65. PMCID: PMC1087722.
21. Ronacher K, Hadley K, Avenant C, Stubsrud E, Simons S S Jr, Louw A, Hapgood J P. Ligand-selective transactivation and transrepression via the glucocorticoid receptor: role of cofactor interaction. Mol Cell Endocrinol. 2009; 299(2):219-31. PMID: 19007848.
22. Jones C L, Gearheart C M, Fosmire S, Delgado-Martin C, Evensen N A, Bride K, Waanders A J, Pais F, Wang J, Bhatla T, Bitterman D S, de Rijk S R, Bourgeois W, Dandekar S, Park E, Burleson T M, Madhusoodhan P P, Teachey D T, Raetz E A, Hermiston M L, Müschen M, Loh M L, Hunger S P, Zhang J, Garabedian M J, Porter C C, Carroll W L. MAPK signaling cascades mediate distinct glucocorticoid resistance mechanisms in pediatric leukemia. Blood. 2015; 126(19):2202-12. PMCID: PMC4635116.
23. Aloia L, Di Stefano B, Di Croce L. Polycomb complexes in stem cells and embryonic development. Development. 2013; 140(12):2525-34. PMID: 23715546.
24. Gao Z, Zhang J, Bonasio R, Strino F, Sawai A, Parisi F, Kluger Y, Reinberg D. PCGF homologs, CBX proteins, and RYBP define functionally distinct PRC1 family complexes. Mol Cell. 2012; 45(3):344-56. PMCID: PMC3293217.
25. Klauke K, Radulović V, Broekhuis M, Weersing E, Zwart E, Olthof S, Ritsema M, Bruggeman S, Wu X, Helin K, Bystrykh L, de Haan G. Polycomb Cbx family members mediate the balance between haematopoietic stem cell self-renewal and differentiation. Nat Cell Biol. 2013; 15(4):353-62. PMID: 23502315.
26. Kimura M, Koseki Y, Yamashita M, Watanabe N, Shimizu C, Katsumoto T, Kitamura T, Taniguchi M, Koseki H, Nakayama T. Regulation of Th2 cell differentiation by mel-18, a mammalian polycomb group gene. Immunity. 2001; 15(2):275-87. PMID: 11520462.
27. Hosokawa H, Kimura M Y, Shinnakasu R, Suzuki A, Miki T, Koseki H, van Lohuizen M, Yamashita M, Nakayama T. Regulation of Th2 cell development by Polycomb group gene bmi-1 through the stabilization of GATA3. J Immunol. 2006; 177(11):7656-64. PMID: 17114435.
28. Yamashita M, Kuwahara M, Suzuki A, Hirahara K, Shinnakasu R, Hosokawa H, Hasegawa A, Motohashi S, Iwama A, Nakayama T. Bmi1 regulates memory CD4 T cell survival via repression of the Noxa gene. J Exp Med. 2008; 205(5):1109-20. PMCID: PMC2373843.
29. Wu H A, Balsbaugh J L, Chandler H, Georgilis A, Zullow H, Shabanowitz J, Hunt D F, Gil J, Peters G, Bernstein E. Mitogen-activated protein kinase signaling mediates phosphorylation of polycomb ortholog Cbx7. J Biol Chem. 2013; 288(51):36398-408. PMCID: PMC3868753.
30. Pallante P, Sepe R, Federico A, Forzati F, Bianco M, Fusco A. CBX7 modulates the expression of genes critical for cancer progression. PLoS One. 2014; 9(5):e98295. PMCID: PMC4035280.
31. Goplen N, Karim M Z, Liang Q, Gorska M M, Rozario S, Guo L, Alam R. Combined sensitization of mice to extracts of dust mite, ragweed, and *Aspergillus* species breaks through tolerance and establishes chronic features of asthma. J Allergy Clin Immunol. 2009; 123(4):925-32.e11. PMCID: PMC2683988.
32. Duechs M J, Tilp C, Tomsic C, Gantner F, Erb K J. Development of a novel severe triple allergen asthma model in mice which is resistant to dexamethasone and partially resistant to TLR7 and TLR9 agonist treatment. PLoS One. 2014; 9(3):e91223. PMCID: PMC3949744.
33. Ren C, Morohashi K, Plotnikov A N, Jakoncic J, Smith S G, Li J, Zeng L, Rodriguez Y, Stojanoff V, Walsh M, Zhou M M. Small-molecule modulators of methyl-lysine binding for the CBX7 chromodomain. Chem Biol. 2015; 22(2):161-8. PMCID: PMC4336573.
34. Irvin C, Zafar I, Good J, Rollins D, Christianson C, Gorska M M, Martin R J, Alam R. Increased frequency of dual-positive TH2/TH17 cells in bronchoalveolar lavage fluid characterizes a population of patients with severe asthma. J Allergy Clin Immunol. 2014; 134:1175-1186.e7. PMCID: PMC4254017.

What is claimed is:

1. A method to treat a subject having a steroid resistant disease or condition comprising administering to the subject a CBX7 inhibitor that decreases chromobox homolog 7 (CBX7) activity, wherein the steroid resistant disease or condition is asthma, and wherein the CBX7 inhibitor is MS37452 or UNC3866.

2. The method of claim 1, wherein the step of administering is by an administration route selected from the group consisting of injection, oral, inhalation and topical.

* * * * *